United States Patent [19]
Berka et al.

[11] Patent Number: 5,736,374
[45] Date of Patent: Apr. 7, 1998

[54] INCREASED PRODUCTION OF β-GALACTOSIDASE IN ASPERGILLUS ORYZAE

[75] Inventors: Randy M. Berka, Davis; John A. Hucul, Union City; Michael Ward, San Francisco, all of Calif.

[73] Assignee: Genencor International, Inc., Rochester, N.Y.

[21] Appl. No.: 596,985

[22] Filed: Feb. 5, 1996

Related U.S. Application Data

[63] Continuation of Ser. No. 267,631, Jun. 29, 1994, abandoned.

[51] Int. Cl.$^6$ .............................. C12N 9/38; C12N 1/14; C12N 15/00; C07H 21/04
[52] U.S. Cl. ................ 435/207; 435/254.11; 435/254.3; 435/320.1; 536/23.2
[58] Field of Search .............................. 435/207, 254.11, 435/254.3, 320.1; 536/23.2

[56] References Cited

U.S. PATENT DOCUMENTS

| | | | |
|---|---|---|---|
| 3,919,049 | 11/1975 | Kiuchi et al. | 195/66 |
| 4,885,249 | 12/1989 | Buxton et al. | 435/172.3 |

FOREIGN PATENT DOCUMENTS

| | | |
|---|---|---|
| 63-301794 | 12/1988 | Japan . |
| WO90/10703 | 9/1990 | WIPO . |

OTHER PUBLICATIONS

Vita et al. 1990 Lymphokine Res. 9:67–79.
Kobayashi, T. et al. (1976) Chem. Abstracts, vol. 85, No. 3, p. 509, Abstract No. 19084g.
van Hartingsveldt, W., et al., Gene, 127:87–94 (1993).
Schmidt, B.F., et al., J. Bacteriol. Feb. 1989, vol. 171, No. 2, pp. 625–635.
Kumar, V., et al., Bio./Technology, vol. 10, Jan. 1992, pp. 82–85.
The Lancet, vol. 338, Sep. 14, 1991, pp. 663–664.
Tanaka, Y., et al., J. Biochem, 77:241–247 (1975).
van Hartingsveldt, W., et al., Mol. Gen. Genet (1987) 206:71–75.
de Ruiter–Jacobs, Y.M.J.T., et al., Curr. Genet (1989) 16:159–163.
Mattern, I.E., et al., Mol. Gen. Genet., (1987) 210:460–461.
Campbell, E.I., et al., Curr. Genet. (1989) 16:53–56.
Roehr, M., Kubicek, C.P., Kominek, J. (1992) (Bennett, J.W. and Klich, M.A., eds.) pp. 116–119.
Butterworth–Heinemann, Stoneham, M.A. and Lockwood, L.B. (1979) *Microbial Technology*, vol. 1, 2nd ed. (Peppler, H.J., ed.) pp. 356–387, Academic Press, New York.
Yoshida, H., Araki, K., Kawai, M. (1988) *Agric. Biol. Chem.* 52:951–955.

*Primary Examiner*—Robert A. Wax
*Assistant Examiner*—Lisa J. Hobbs
*Attorney, Agent, or Firm*—Debra J. Glaister

[57] ABSTRACT

Novel methods are disclosed for the enhanced expression and secretion of lactase from filamentous fungi. Specifically the novel processes cause enhanced production of lactase from an Aspergillus and preferably enhanced production of A. oryzae lactase from A. oryzae host strains transformed with necessary DNA. Also described are the DNA sequence encoding the lactase gene from A. oryzae and the deduced amino acid sequence of the lactase therefrom.

10 Claims, 7 Drawing Sheets

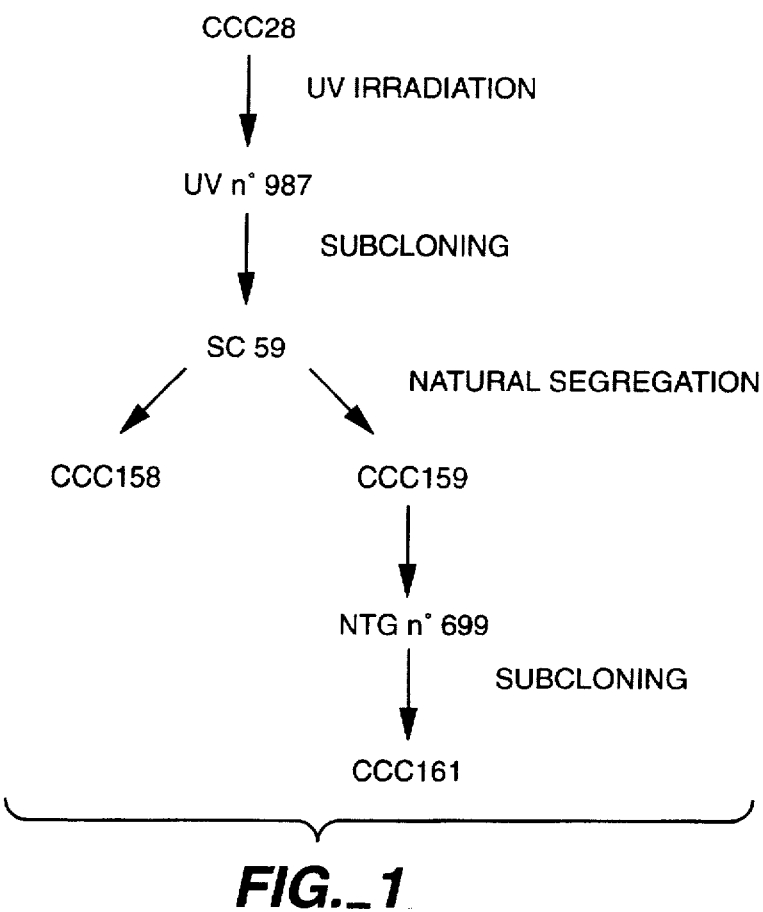
FIG._1
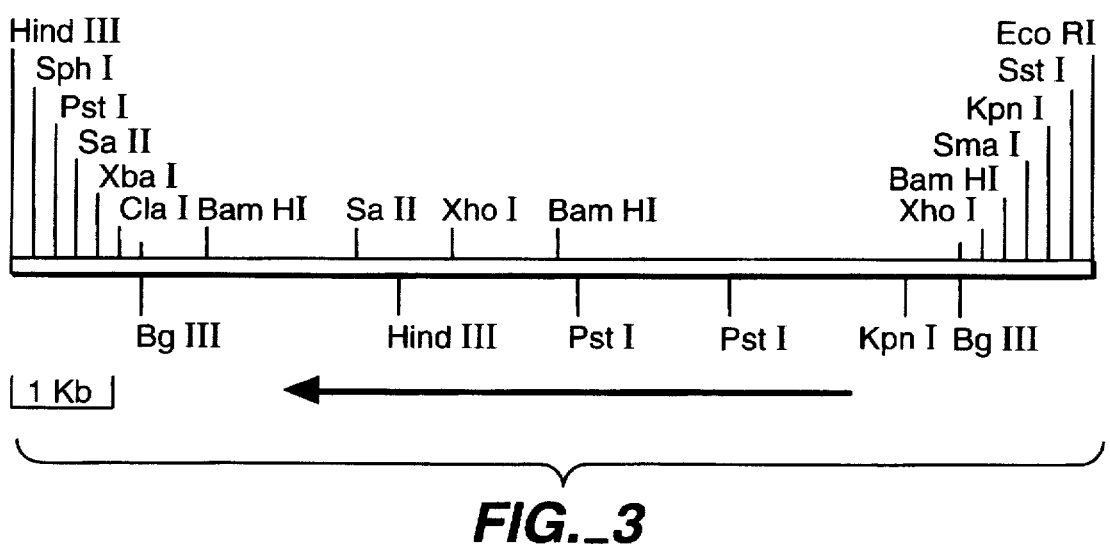
FIG._3

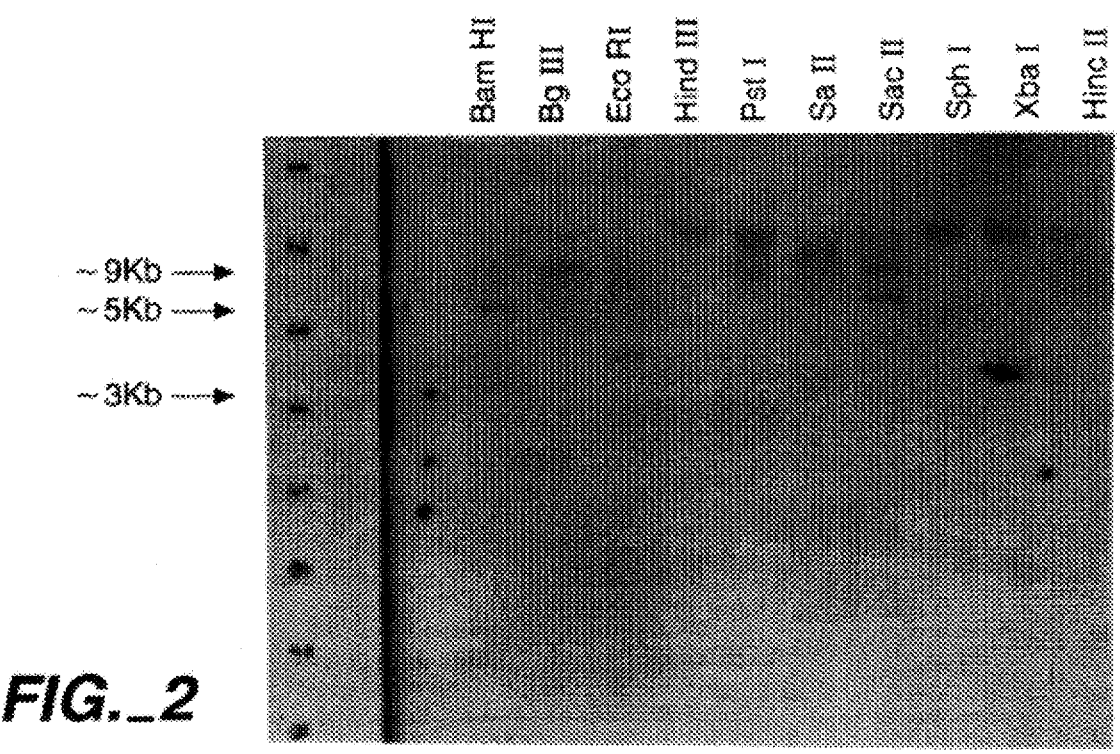
FIG._2
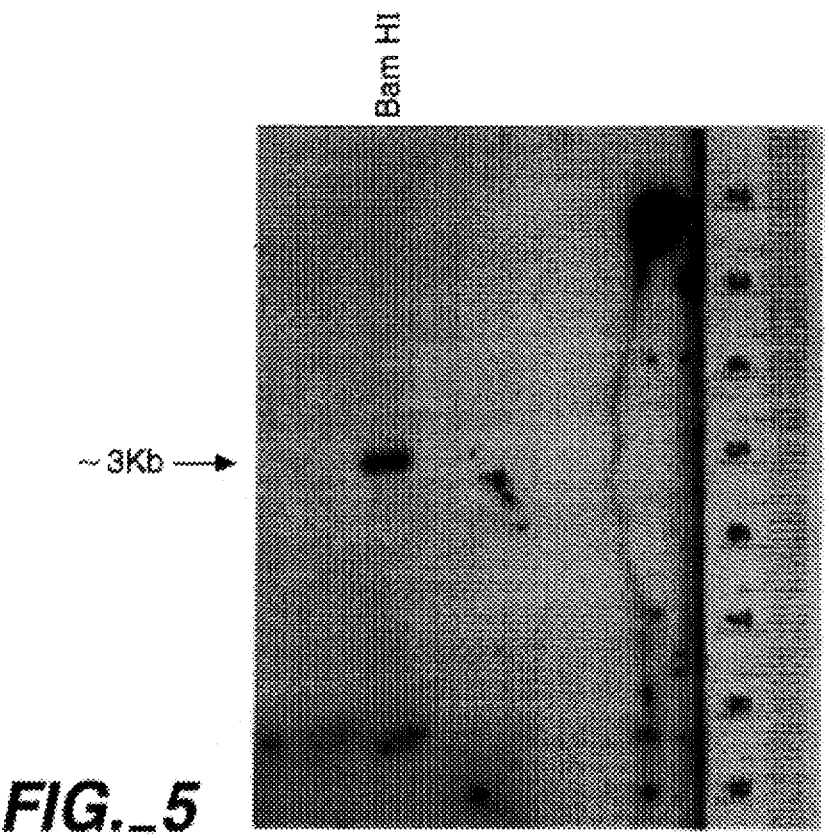
FIG._5

```
CCCCATCTGA TTTGGATGTT AATGGTGCTT TGACCAGCCG TGGTCATTGT      50
GGCTGGTTTG TTTGTATACA GCTCCACGAC CTCTACATGA TGTTAAGATG     100
AAATCGTACG GGACTCCACT TTCGGCTAAG GACTCTATTG GACCATTCCC     150
TCCTCTATAC ATCATCAACG CAAGGTGTCG ACATTTTAA TTAACGAAGT      200
CGGTTATTTT TGACTATTTA TCCTTTCAAT CTTACTTATA TTCGTGCAAT     250
TGCCCCCGAA ACATGGGAAA TCTGCTGTAA GCTCTCACTG GGGTTCTTCT     300
GCAGCACGGC ACCATGAAGC TCCTCTCTGT TGCTGCTGTT GCCTTGCTGG     350
CGGCACAGGC AGCGGGTGCT TCCATCAAGC ATCGTCTCAA TGGCTTCACG     400
ATCCTGGAAC ATCCGGATCC GGCGAAAAGA GACTTGCTGC AAGACATTGT     450
Intron 1
ATGTCGTCAT CAAATCTGAA TCACTAGCTA TGCTCCATAG TGATTATGTA     500
AACATACTGA CCCTCTGCAG GTTACATGGG ATGACAAATC TCTGTTCATC     550
AATGGAGAGA GGATTATGTT ATTCAGCGGA GAAGTGCATC CTTTCAGGTA     600
Intron 2
CACTAGCCCC GCGTACTTTA TGGTTTAATT CTGATGAAAA CAGATTGCCA     650
GTACCTTCGC TTTGGCTTGA TATCTTCCAC AAGATCAGAG CTCTTGGTTT     700
CAACTGTGTA TCTTTCTATA TTGATTGGGC TCTTCTGGAG GGAAAGCCTG     750
GCGACTACAG AGCAGAAGGC ATCTTTGCTC TGGAACCCTT CTTTGATGCA     800
GCCAAGGAAG CAGGCATTTA TCTGATCGCC CGCCCCGGTT CGTACATCAA     850
TGCCGAGGTC TCAGGCGGTG GCTTCCCTGG ATGGTTGCAG AGGGTCAATG     900
GCACTCTTCG CTCGTCTGAT GAGCCATTCC TTAAAGCTAC TGATAAGTAT     950
Intron 3
GGGCTCATTG ATGAGCTACT TCAGACACTT GCTTACAGTG TGATTTTAGC    1000
TATATCGCCA ATGCCGCTGC TGCCGTGGCG AAGGCTCAAA TCACGAATGG    1050
AGGGCCAGTA ATTCTCTACC AGCCCGAAAA CGAATACAGC GGTGGCTGCT    1100
GCGGTGTCAA ATACACCGAT GCAGACTACA TGCAGTATGT TATGGATCAG    1150
GCCCGGAAGG CTGACATTGT TGTACCTTTC ATCAGCAACG ATGCCTCACC    1200
TTCTGGGCAC AATGCTCCTG GAAGTGGAAC GGGCGCTGTT GATATTTATG    1250
                                 Intron 4
GTCACGATAG CTATCCGTAA GTTATTCTGC ATATGAGCTC CTTTCTTTTA    1300
GAGATTTTCC GTTTGACGGC AACTGACATT TCCCTAGCCT CGGCTTTGAT    1350
       Intron 5
TGCGTATGTT CTATCCTGCG AGCGAGATTG AATACTTCTG ACGTATATAG    1400
GCAAACCCAT CCGTATGGCC CGAGGGTAAA CTGCCCGACA ACTTCCGCAC    1450
GCTCCATCTT GAGCAGAGCC CATCGGCTCC GTATTCACTT CTTGAGGTAA    1500
Intron 6
GTTACTACTC AGCCTCGAGG ACTAGTAATG TGTCTCACTG TTTTCTAGTT    1550
CCAAGCGGGT                                                1560
```

*FIG._4A*

```
GCTTTCGACC CATGGGGTGG ACCCGGCTTT GAAAAATGCT ATGCCCTCGT    1610
TAACCACGAA TTCTCGAGAG TTTTCTATAG GAACGACTTG AGTTTCGGAG    1660
                                 Intron 7
TTTCTACCTT TAACTTATAC ATGGTATGGT CTATTCATAT CTCTGGAACA    1710
TACATCGCGC TGACAATATA TAGACTTTCG GCGGAACAAA CTGGGGTAAC    1760
CTCGGACATC CCGGTGGATA TACATCCTAC GACTACGGAT CGCCTATAAC    1810
TGAAACGCGA AACGTTACAC GGGAGAAGTA CAGCGACATA AGCTCCTTG     1860
CCAACTTTGT CAAAGCATCG CCATCCTATC TCACCGCTAC TCCCAGAAAC    1910
CTGACTACTG GTGTTTACAC AGACACATCT GACCTGGCTG TCACCCCGTT    1960
AATTGGTGAT AGTCCAGGCT CATTCTTCGT GGTCAGACAT ACGGACTATT    2010
CCAGCCAAGA GTCAACCTCG TACAAACTTA AGCTTCCTAC CAGTGCTGGT    2060
AACCTGACTA TTCCCCAGCT GGAGGGCACT CTAAGTCTCA ACGGACGTGA    2110
CTCAAAAATT CATGTTGTTG ATTATAATGT GTCTGGAACG AACATTATCT    2160
ATTCGACAGC TGAAGTCTTC ACCTGGAAGA AGTTTGACGG TAACAAGGTC    2210
CTGGTGTTAT ACGGCGGACC GAAGGAACAC CATGAATTGG CCATTGCCTC    2260
CAAGTCAAAT GTGACCATCA TCGAAGGTTC GGACTCTGGA ATTGTCTCAA    2310
CGAGGAAGGG CAGCTCTGTT ATCATTGGCT GGGATGTCTC TTCTACTCGT    2360
CGCATCGTTC AAGTCGGTGA CTTGAGAGTG TTCCTGCTTG GTAAGTAAAT    2410
 Intron 8
TCACAAGAAA CTCGCGTTCA CGACTAATGA ATCCACAGAT AGGAACTCTG    2460
CTTACAACTA CTGGGTCCCC GAACTCCCCA CAGAAGGTAC TTCTCCCGGG    2510
TTCAGCACTT CGAAGACGAC CGCCTCCTCC ATTATTGTGA AGGCTGGCTA    2560
CCTCCTCCGA GGCGCTCACC TTGATGGTGC TGATCTTCAT CTTACTGCTG    2610
ATTTCAATGC CACCACCCCG ATTGAAGTGA TCGGTGCTCC AACAGGCGCT    2660
                                               Sal I
AAGAATCTGT TCGTGAATGG TGAAAAGGCT AGCCACACAG TCGACAAGAA    2710
CGGCATCTGG AGCAGTGAGG TCAAGTACGC GGCTCCAGAG ATCAAGCTCC    2760
CCGGTTTGAA GGATTTGGAC TGGAAGTATC TGGACACGCT TCCCGAAATT    2810
AAGTCTTCCT ATGATGACTC GGCCTGGGTT TCGGCAGACC TTCCAAAGAC    2860
AAAGAACACT CACCGTCCTC TTGACACACC AACATCGCTA TACTCCTCTG    2910
ACTATGGCTT CCACACTGGC TACCTGATCT ACAGGGGTCA CTTCGTTGCC    2960
AACGGTAAGG AAAGCGAATT TTTTATTCGC ACACAAGGCG GTAGCGCATT    3010
CGGAAGTTCC GTATGGCTGA ACGAGACGTA TCTGGGCTCT TGGACTGGTC    3060
CCGATTATAC GATGGACGGT AACTCTACCT ACAAGCTATC TCAGCTGGAG    3110
TCGGGCAAGA ATTACGTCAT CACTGTGGTT ATTGATAACC TGGGTCTCGA    3160
CGAGAATTGG ACGGTCGGCG                                    3180
```

*FIG._4B*

```
AGGAAACCAT GAAGAATCCT CGTGGTATTC TTAGCTACAA GCTGAGCGGA      3230
CAAGACGCCA GCGCAATCAC CTGGAAGCTC ACTGGTAACC TCGGAGGAGA      3280
AGACTACCAG GATAAGGTTA GAGGACCTCT CAACGAAGGT GGACTGTACG      3330
CAGAGCGCCA GGGTTTCCAT CAGCCTCAGC CTCCAAGCGA CTCCTGGGAG      3380
TCGGGCAGTC CCCTTGAAGG GCTGTCGAAG CCGGGTATCG GATTCTACAC      3430
TGCCCAGTTC GACCTTGACC TCCCGAAGGG GTGGGATGTG CCGCTGTACT      3480
TCAACTTTGG CAACAACACC CAGGCGGCTC GGGCC                      3515
```

FIG._4C

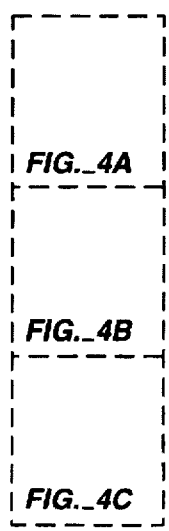

FIG._4

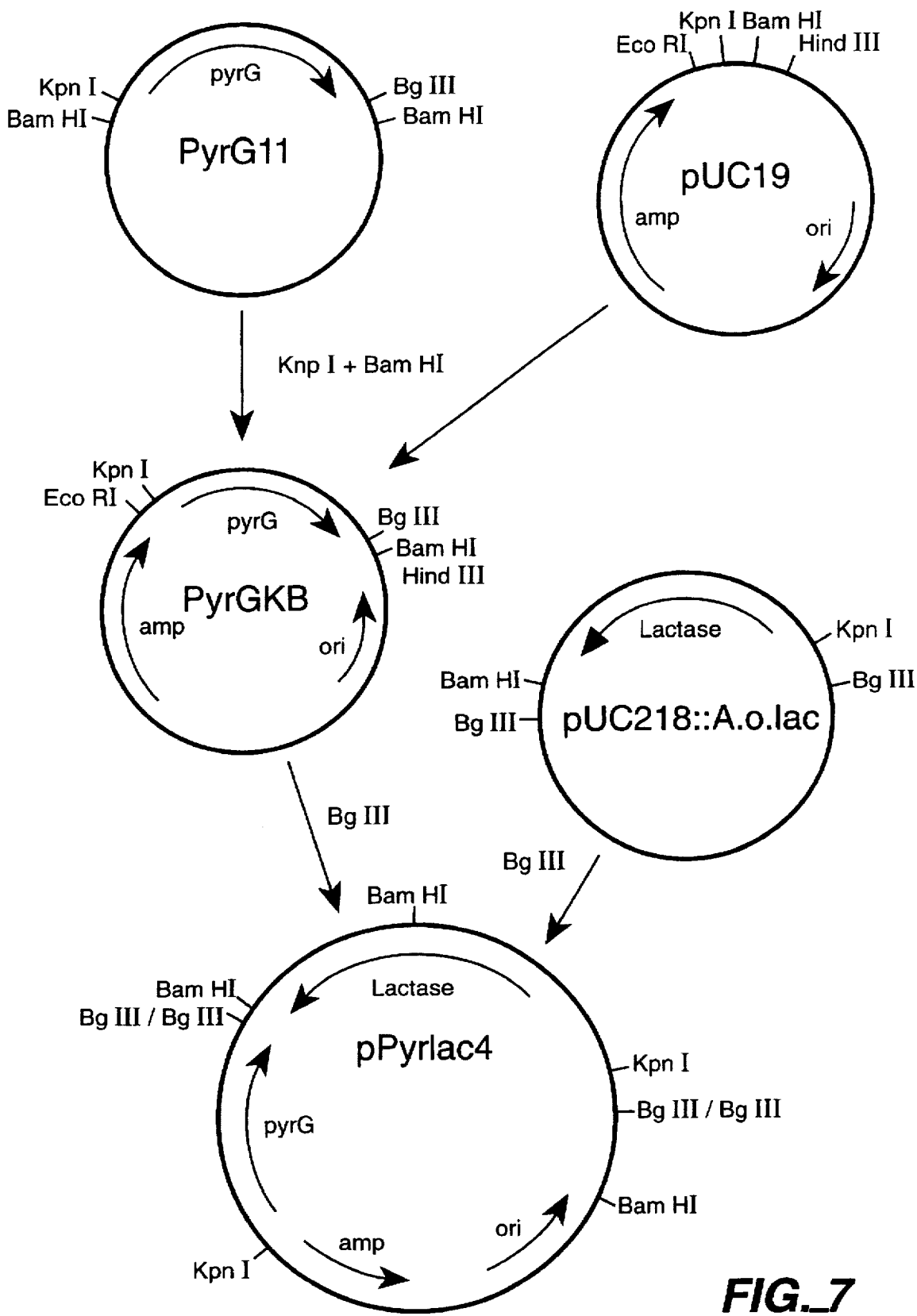
FIG._7

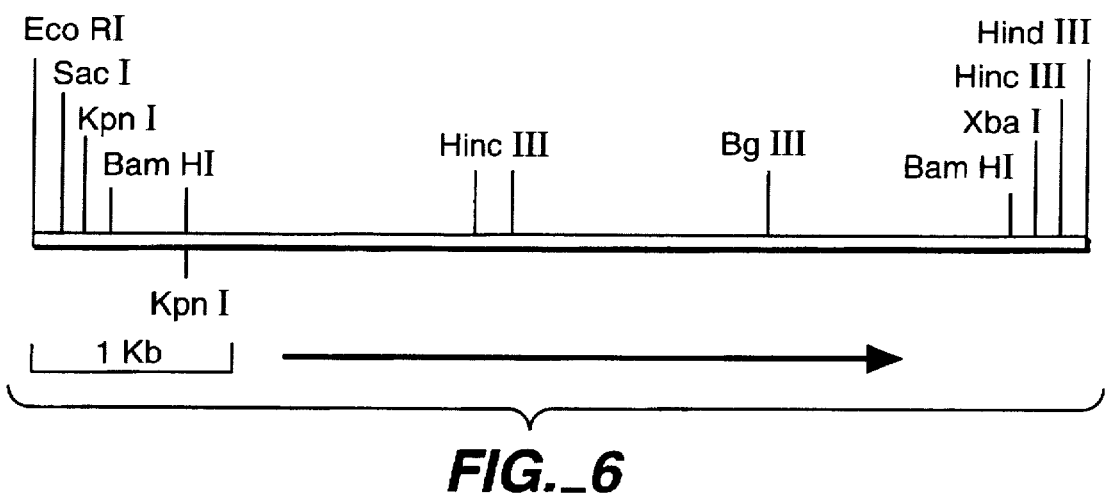
FIG._6
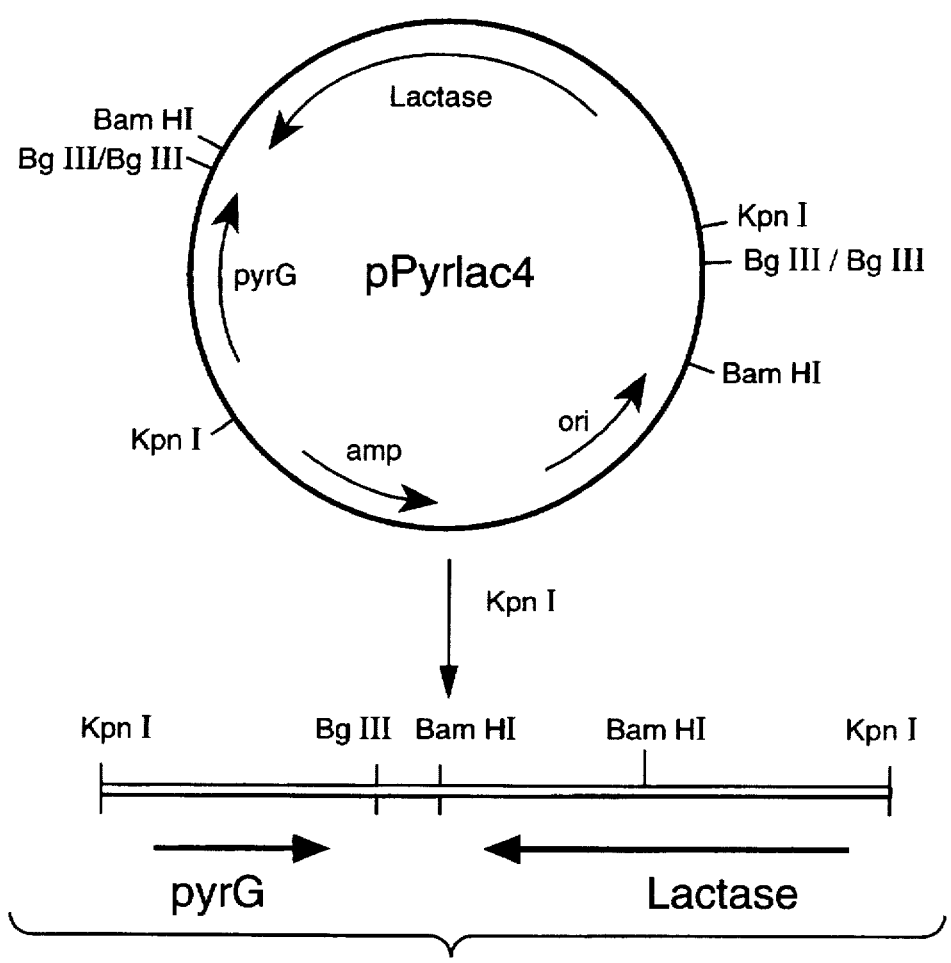
FIG._8

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 3515 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
CCCCATCTGA TTTGGATGTT AATGGTGCTT TGACCAGCCG TGGTCATTGT GGCTGGTTTG      60
TTTGTATACA GCTCCACGAC CTCTACATGA TGTTAAGATG AAATCGTACG GGACTCCACT     120
TTCGGCTAAG GACTCTATTG GACCATTCCC TCCTCTATAC ATCATCAACG CAAGGTGTCG     180
GACATTTTAA TTAACGAAGT CGGTTATTTT TGACTATTTA TCCTTTCAAT CTTACTTATA     240
TTCGTGCAAT TGCCCCCGAA ACATGGGAAA TCTGCTGTAA GCTCTCACTG GGGTTCTTCT     300
GCAGCACGGC ACCATGAAGC TCCTCTCTGT TGCTGCTGTT GCCTTGCTGG CGGCACAGGC     360
AGCGGGTGCT TCCATCAAGC ATCGTCTCAA TGGCTTCACG ATCCTGGAAC ATCCGGATCC     420
GGCGAAAAGA GACTTGCTGC AAGACATTGT ATGTCGTCAT CAAATCTGAA TCACTAGCTA     480
TGCTCCATAG TGATTATGTA AACATACTGA CCCTCTGCAG GTTACATGGG ATGACAAATC     540
TCTGTTCATC AATGGAGAGA GGATTATGTT ATTCAGCGGA GAAGTGCATC CTTTCAGGTA     600
CACTAGCCCC GCGTACTTTA TGGTTTAATT CTGATGAAAA CAGATTGCCA GTACCTTCGC     660
TTTGGCTTGA TATCTTCCAC AAGATCAGAG CTCTTGGTTT CAACTGTGTA TCTTTCTATA     720
TTGATTGGGC TCTTCTGGAG GGAAAGCCTG GCGACTACAG AGCAGAAGGC ATCTTTGCTC     780
TGGAACCCTT CTTTGATGCA GCCAAGGAAG CAGGCATTTA TCTGATCGCC CGCCCCGGTT     840
CGTACATCAA TGCCGAGGTC TCAGGCGGTG GCTTCCCTGG ATGGTTGCAG AGGGTCAATG     900
GCACTCTTCG CTCGTCTGAT GAGCCATTCC TTAAAGCTAC TGATAAGTAT GGGCTCATTG     960
ATGAGCTACT TCAGACACTT GCTTACAGTG TGATTTTAGC TATATCGCCA ATGCCGCTGC    1020
TGCCGTGGCG AAGGCTCAAA TCACGAATGG AGGGCCAGTA ATTCTCTACC AGCCCGAAAA    1080
CGAATACAGC GGTGGCTGCT GCGGTGTCAA ATACACCGAT GCAGACTACA TGCAGTATGT    1140
TATGGATCAG GCCCGGAAGG CTGACATTGT TGTACCTTTC ATCAGCAACG ATGCCTCACC    1200
TTCTGGGCAC AATGCTCCTG GAAGTGGAAC GGGCGCTGTT GATATTTATG GTCACGATAG    1260
CTATCCGTAA GTTATTCTGC ATATGAGCTC CTTTCTTTTA GAGATTTCC GTTGACGGC     1320
AACTGACATT TCCCTAGCCT CGGCTTTGAT TGCGTATGTT CTATCCTGCG AGCGAGATTG    1380
AATACTTCTG ACGTATATAG GCAAACCCAT CCGTATGGCC CGAGGGTAAA CTGCCCGACA    1440
ACTTCCGCAC GCTCCATCTT GAGCAGAGCC CATCGGCTCC GTATTCACTT CTTGAGGTAA    1500
GTTACTACTC AGCCTCGAGG ACTAGTAATG TGTCTCACTG TTTTCTAGTT CCAAGCGGGT    1560
GCTTTCGACC CATGGGGTGG ACCCGGCTTT GAAAAATGCT ATGCCCTCGT TAACCACGAA    1620
TTCTCGAGAG TTTTCTATAG GAACGACTTG AGTTTCGGAG TTTCTACCTT TAACTTATAC    1680
```

```
ATGGTATGGT CTATTCATAT CTCTGGAACA TACATCGCGC TGACAATATA TAGACTTTCG    1740
GCGGAACAAA CTGGGGTAAC CTCGGACATC CCGGTGGATA TACATCCTAC GACTACGGAT    1800
CGCCTATAAC TGAAACGCGA AACGTTACAC GGGAGAAGTA CAGCGACATA AAGCTCCTTG    1860
CCAACTTTGT CAAAGCATCG CCATCCTATC TCACCGCTAC TCCCAGAAAC CTGACTACTG    1920
GTGTTTACAC AGACACATCT GACCTGGCTG TCACCCCGTT AATTGGTGAT AGTCCAGGCT    1980
CATTCTTCGT GGTCAGACAT ACGGACTATT CCAGCCAAGA GTCAACCTCG TACAAACTTA    2040
AGCTTCCTAC CAGTGCTGGT AACCTGACTA TTCCCCAGCT GGAGGGCACT CTAAGTCTCA    2100
ACGGACGTGA CTCAAAAATT CATGTTGTTG ATTATAATGT GTCTGGAACG AACATTATCT    2160
ATTCGACAGC TGAAGTCTTC ACCTGGAAGA AGTTTGACGG TAACAAGGTC CTGGTGTTAT    2220
ACGGCGGACC GAAGGAACAC CATGAATTGG CCATTGCCTC CAAGTCAAAT GTGACCATCA    2280
TCGAAGGTTC GGACTCTGGA ATTGTCTCAA CGAGGAAGGG CAGCTCTGTT ATCATTGGCT    2340
GGGATGTCTC TTCTACTCGT CGCATCGTTC AAGTCGGTGA CTTGAGAGTG TTCCTGCTTG    2400
GTAAGTAAAT TCACAAGAAA CTCGCGTTCA CGACTAATGA ATCCACAGAT AGGAACTCTG    2460
CTTACAACTA CTGGGTCCCC GAACTCCCCA CAGAAGGTAC TTCTCCCGGG TTCAGCACTT    2520
CGAAGACGAC CGCCTCCTCC ATTATTGTGA AGGCTGGCTA CCTCCTCCGA GGCGCTCACC    2580
TTGATGGTGC TGATCTTCAT CTTACTGCTG ATTTCAATGC CACCACCCCG ATTGAAGTGA    2640
TCGGTGCTCC AACAGGCGCT AAGAATCTGT TCGTGAATGG TGAAAAGGCT AGCCACACAG    2700
TCGACAAGAA CGGCATCTGG AGCAGTGAGG TCAAGTACGC GGCTCCAGAG ATCAAGCTCC    2760
CCGGTTTGAA GGATTTGGAC TGGAAGTATC TGGACACGCT TCCCGAAATT AAGTCTTCCT    2820
ATGATGACTC GGCCTGGGTT TCGGCAGACC TTCCAAAGAC AAAGAACACT CACCGTCCTC    2880
TTGACACACC AACATCGCTA TACTCCTCTG ACTATGGCTT CCACACTGGC TACCTGATCT    2940
ACAGGGGTCA CTTCGTTGCC AACGGTAAGG AAAGCGAATT TTTTATTCGC ACACAAGGCG    3000
GTAGCGCATT CGGAAGTTCC GTATGGCTGA ACGAGACGTA TCTGGGCTCT TGGACTGGTC    3060
CCGATTATAC GATGGACGGT AACTCTACCT ACAAGCTATC TCAGCTGGAG TCGGGCAAGA    3120
ATTACGTCAT CACTGTGGTT ATTGATAACC TGGGTCTCGA CGAGAATTGG ACGGTCGGCG    3180
AGGAAACCAT GAAGAATCCT CGTGGTATTC TTAGCTACAA GCTGAGCGGA CAAGACGCCA    3240
GCGCAATCAC CTGGAAGCTC ACTGGTAACC TCGGAGGAGA AGACTACCAG GATAAGGTTA    3300
GAGGACCTCT CAACGAAGGT GGACTGTACG CAGAGCGCCA GGGTTTCCAT CAGCCTCAGC    3360
CTCCAAGCGA CTCCTGGGAG TCGGGCAGTC CCTTGAAGG GCTGTCGAAG CCGGGTATCG    3420
GATTCTACAC TGCCCAGTTC GACCTTGACC TCCCGAAGGG GTGGGATGTG CCGCTGTACT    3480
TCAACTTTGG CAACAACACC CAGGCGGCTC GGGCC                               3515
```

( 2 ) INFORMATION FOR SEQ ID NO:2:

( i ) SEQUENCE CHARACTERISTICS:
        ( A ) LENGTH: 911 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

```
Met Lys Leu Leu Ser Val Ala Ala Val Ala Leu Leu Ala Ala Gln Ala
 1               5                  10                  15

Ala Gly Ala Ser Ile Lys His Arg Leu Asn Gly Phe Thr Ile Leu Glu
```

-continued

```
              20                        25                        30
His Pro Asp Pro Ala Lys Arg Asp Leu Leu Gln Asp Ile Val Thr Trp
         35                     40                  45
Asp Asp Lys Ser Leu Phe Ile Asn Gly Glu Arg Ile Met Leu Phe Ser
     50                  55                  60
Gly Glu Val His Pro Phe Arg Leu Pro Val Pro Ser Leu Trp Leu Asp
 65                  70                  75                   80
Ile Phe His Lys Ile Arg Ala Leu Gly Phe Asn Cys Val Ser Phe Tyr
             85                      90                      95
Ile Asp Trp Ala Leu Leu Glu Gly Lys Pro Gly Asp Tyr Arg Ala Glu
             100                 105             110
Gly Ile Phe Ala Leu Glu Pro Phe Phe Asp Ala Ala Lys Glu Ala Gly
             115                 120             125
Ile Tyr Leu Ile Ala Arg Pro Gly Ser Tyr Ile Asn Ala Glu Val Ser
         130             135                 140
Gly Gly Gly Phe Pro Gly Trp Leu Gln Arg Val Asn Gly Thr Leu Arg
 145                 150                 155                 160
Ser Ser Asp Glu Pro Phe Leu Lys Ala Thr Asp Asn Tyr Ile Ala Asn
             165                 170                 175
Ala Ala Ala Ala Val Ala Lys Ala Gln Ile Thr Asn Gly Gly Pro Val
             180             185                 190
Ile Leu Tyr Gln Pro Glu Asn Glu Tyr Ser Gly Gly Cys Cys Gly Val
         195                 200                 205
Lys Tyr Thr Asp Ala Asp Tyr Met Gln Tyr Val Met Asp Gln Ala Arg
     210                 215                 220
Lys Ala Asp Ile Val Val Pro Phe Ile Ser Asn Asp Ala Ser Pro Ser
 225                 230                 235                 240
Gly His Asn Ala Pro Gly Ser Gly Thr Gly Ala Val Asp Ile Tyr Gly
             245                 250                 255
His Asp Ser Tyr Pro Leu Gly Phe Asp Cys Ala Asn Pro Ser Val Trp
             260                 265                 270
Pro Glu Gly Lys Leu Pro Asp Asn Phe Arg Thr Leu His Leu Glu Gln
         275                 280                 285
Ser Pro Ser Ala Pro Tyr Ser Leu Leu Glu Phe Gln Ala Gly Ala Phe
     290                 295                 300
Asp Pro Trp Gly Gly Pro Gly Phe Glu Lys Cys Tyr Ala Leu Val Asn
 305                 310                 315                 320
His Glu Phe Ser Arg Val Phe Tyr Arg Asn Asp Leu Ser Phe Gly Val
             325                 330                 335
Ser Thr Phe Asn Leu Tyr Met Thr Phe Gly Gly Thr Asn Trp Gly Asn
             340                 345                 350
Leu Gly His Pro Gly Gly Tyr Thr Ser Tyr Asp Tyr Gly Ser Pro Ile
             355                 360                 365
Thr Glu Thr Arg Asn Val Thr Arg Glu Lys Tyr Ser Asp Ile Lys Leu
         370                 375                 380
Leu Ala Asn Phe Val Lys Ala Ser Pro Ser Tyr Leu Thr Ala Thr Pro
 385                 390                 395                 400
Arg Asn Leu Thr Thr Gly Val Tyr Thr Asp Thr Ser Asp Leu Ala Val
             405                 410                 415
Thr Pro Leu Ile Gly Asp Ser Pro Gly Ser Phe Phe Val Val Arg His
             420                 425                 430
Thr Asp Tyr Ser Ser Gln Glu Ser Thr Ser Tyr Lys Leu Lys Leu Pro
         435                 440                 445
```

```
Thr Ser Ala Gly Asn Leu Thr Ile Pro Gln Leu Glu Gly Thr Leu Ser
    450                 455                 460
Leu Asn Gly Arg Asp Ser Lys Ile His Val Val Asp Tyr Asn Val Ser
465                 470                 475                 480
Gly Thr Asn Ile Ile Tyr Ser Thr Ala Glu Val Phe Thr Trp Lys Lys
                 485                 490                 495
Phe Asp Gly Asn Lys Val Leu Val Leu Tyr Gly Gly Pro Lys Glu His
                500                 505                 510
His Glu Leu Ala Ile Ala Ser Lys Ser Asn Val Thr Ile Ile Glu Gly
            515                 520                 525
Ser Asp Ser Gly Ile Val Ser Thr Arg Lys Gly Ser Ser Val Ile Ile
    530                 535                 540
Gly Trp Asp Val Ser Ser Thr Arg Arg Ile Val Gln Val Gly Asp Leu
545                 550                 555                 560
Arg Val Phe Leu Leu Gly Lys Asn Ser Ala Tyr Asn Tyr Trp Val Pro
                565                 570                 575
Glu Leu Pro Thr Glu Gly Thr Ser Pro Gly Phe Ser Thr Ser Lys Thr
            580                 585                 590
Thr Ala Ser Ser Ile Ile Val Lys Ala Gly Tyr Leu Leu Arg Gly Ala
    595                 600                 605
His Leu Asp Gly Ala Asp Leu His Leu Thr Ala Asp Phe Asn Ala Thr
    610                 615                 620
Thr Pro Ile Glu Val Ile Gly Ala Pro Thr Gly Ala Lys Asn Leu Phe
625                 630                 635                 640
Val Asn Gly Glu Lys Ala Ser His Thr Val Asp Lys Asn Gly Ile Trp
                645                 650                 655
Ser Ser Glu Val Lys Tyr Ala Ala Pro Glu Ile Lys Leu Pro Gly Leu
            660                 665                 670
Lys Asp Leu Asp Trp Lys Tyr Leu Asp Thr Leu Pro Glu Ile Lys Ser
    675                 680                 685
Ser Tyr Asp Asp Ser Ala Trp Val Ser Ala Asp Leu Pro Lys Thr Lys
    690                 695                 700
Asn Thr His Arg Pro Leu Asp Thr Pro Thr Ser Leu Tyr Ser Ser Asp
705                 710                 715                 720
Tyr Gly Phe His Thr Gly Tyr Leu Ile Tyr Arg Gly His Phe Val Ala
                725                 730                 735
Asn Gly Lys Glu Ser Glu Phe Leu Ile Arg Thr Gln Gly Gly Ser Ala
            740                 745                 750
Phe Gly Ser Ser Val Trp Leu Asn Glu Thr Tyr Leu Gly Ser Trp Thr
    755                 760                 765
Gly Ala Asp Tyr Thr Met Asp Gly Asn Ser Thr Tyr Lys Leu Ser Gln
    770                 775                 780
Leu Glu Ser Gly Asn Tyr His Val Ile Thr Val Val Ile Asp Asn Leu
785                 790                 795                 800
Gly Leu Asp Glu Asn Trp Thr Val Gly Glu Glu Thr Met Lys Asn Pro
                805                 810                 815
Arg Gly Ile Leu Ser Tyr Lys Leu Ser Gly Gln Asp Ala Ser Ala Ile
            820                 825                 830
Thr Trp Lys Leu Thr Gly Asn Leu Gly Gly Glu Asp Tyr Gln Asp Lys
    835                 840                 845
Val Arg Gly Pro Leu Asn Glu Gly Gly Leu Tyr Ala Glu Arg Gln Gly
    850                 855                 860
Phe His Gln Pro Gln Pro Pro Ser Asp Ser Trp Glu Ser Gly Ser Pro
865                 870                 875                 880
```

```
          Leu  Glu  Gly  Leu  Ser  Lys  Pro  Gly  Ile  Gly  Phe  Tyr  Thr  Ala  Gln  Phe
                              885                      890                      895

Asp  Leu  Asp  Leu  Pro  Lys  Arg  Ala  Glu  Gly  Pro  Ser  Ser  Thr  Ser
                         900                      905                      910
```

( 2 ) INFORMATION FOR SEQ ID NO:3:

( i ) SEQUENCE CHARACTERISTICS:
    ( A ) LENGTH: 19 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:3:

```
          Met  Lys  Leu  Leu  Ser  Val  Ala  Ala  Val  Ala  Leu  Leu  Ala  Ala  Gln  Ala
           1                    5                     10                       15

Ala  Gly  Ala
```

( 2 ) INFORMATION FOR SEQ ID NO:4:

( i ) SEQUENCE CHARACTERISTICS:
    ( A ) LENGTH: 57 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:4:

ATGAAGCTCC TCTCTGTTGC TGCTGTTGCC TTGCTGGCGG CACAGGCAGC GGGTGCT                57

1

INCREASED PRODUCTION OF β-GALACTOSIDASE IN ASPERGILLUS ORYZAE

This is a Continuation of application Ser. No. 08/267,631 filed Jun. 29, 1994, now abandoned.

FIELD OF THE INVENTION

This invention relates to the enhanced production of lactase in *Aspergillus oryzae*. More particularly this invention relates to the enhanced production of Aspergillus lactase in an Aspergillus host cell by transforming such host cell with DNA, comprising a DNA sequence encoding an *Aspergillus oryzae* lactase and additional DNA necessary for the regulation, expression and secretion of the lactase product.

BACKGROUND OF THE INVENTION

Lactose is the main sugar found in milk and whey (about 42%). Whey is the liquid which remains after solids have been removed from cream or milk during cheese production.

The enzyme β-D-galactosidase (β-D-galactosido galactohydrolase, EC 3.2.1.23, also referred to as lactase) hydrolyses the disaccharide lactose to glucose and galactose. The presence of lactose in milk and whey is considered to give rise to several medical problems in certain populations. These medical problems are generally referred to as "lactose intolerance". For example, it is believed that a high percentage of Asians, Africans and Afro-Americans (~90%) and approximately about 5% of white Americans and Western Europeans have a β-galactosidase (lactase) deficiency. (*The Lancet*, Vol. 338, Sep. 14, 1994, p. 663–664.) The effects of a deficiency in the lactase enzyme are typically exhibited as abdominal bloating, rumbling, and/or diarrhea after the ingestion of a lactose containing product such as milk, ice cream or other dairy products. Children may also be susceptible to some type of lactose intolerance, whereby they are unable to convert galactose to glucose. Galactose is accumulated in the blood, and the liver becomes enlarged. This disorder is called galactosemia.

It is believed that 30 to 50 million people suffer from some form of lactose intolerance. Several lactase products are commercially available for the treatment of lactose intolerance, including, for example, Lactaid (commercially available from Johnson & Johnson), Dairy Ease (commercially available from Sterling Winthrop, Inc.) and Lactogest (commercially available from Thompson Medical). These lactase products are typically classified to fall into one of two general categories: low pH optimum (2.5–3.5) lactase for human oral consumption via tablets or capsules; and neutral pH optimum (6.5–7.0) lactase for use as a food additive in milk, cheese, ice cream and *other food products containing lactose or whey. Generally the low pH optimum lactase is produced in fungal organisms by the Koji lactase process. This process is believed to be similar to the Koji process for production of citric acid as described in Roehr, M., Kubicek, C. P., Kominek, J. (1992) (Bennett, J. W. and Klich, M. A., eds.) pp. 116–119; Butterworth-Heinemann, Stoneham, M. A. and Lockwood, L. B. (1979) *Microbial Technology*, Vol. 1, 2nd ed. (Peppler, H. J., ed.) pp. 356–387, Academic Press, New York. The neutral pH lactase is typically produced in yeast such as *Kluyveromyces lactis*, as described in Yoshida, H., Araki, K., Kawai, M. (1988) *Agric. Biol. Chem.* 52:951–955.

Since existing production methods may be associated with industrial hygiene or regulatory/safety concerns and/or are not considered cost effective, there is a need to develop a safe, cost effective production system for lactase. It is therefore an object of the present invention to provide methods for the enhanced production of lactase which can be administered to those people suffering from such lactose intolerance. The lactase of this invention may be administered to a mammal suffering from lactose intolerance by any method known, such as in pills, drops or in milk or dairy products actually containing the enzyme.

SUMMARY OF THE INVENTION

Accordingly, an object of this invention is to provide a process for the enhanced production of lactase. Therefore, one embodiment of this invention comprises a novel process for the enhanced production of lactase from an Aspergillus strain (preferably *A. oryzae*). The methods of this invention provide for the transformation of Aspergillus with DNA, including a DNA sequence encoding a lactase gene (preferably an Aspergillus lactase and most preferably the *Aspergillus oryzae* lactase), and DNA encoding a signal sequence which is functional in a secretory system in such Aspergillus strain and which is operably linked to the DNA sequence encoding the lactase gene. Such signal sequences may be the signal sequence normally associated with the lactase or may be derived from other sources.

Any lactase gene expressible in a filamentous fungi can be used in the present invention. The lactase gene from *Lactobacillus bulgaricus* was cloned and expressed in *E. coli* (Schmidt, B. F., et al., *Journal of Bacteriology*, Feb. 1989, p. 625–635). The lactase gene and cDNA sequence from *A. niger* is known (Kumar, V., et al., *Bio/Technology* 10:82–85, 1992). The *A. oryzae* lactase gene was cloned and partially sequenced by applicants and its expression in *A. oryzae* is detailed herein. The C-terminal portion of the gene is still being sequenced. Thus, another embodiment of the present invention relates to a DNA fragment (gene) encoding all or substantially all of the lactase gene from *A. oryzae* (Seq ID No 1) and the amino acid sequence of the lactase protein (Seq ID No 2) encoded for by such gene having lactose hydrolytic activity. It should be understood that although the entire lactase gene has not been sequenced, one skilled in the art, following the teachings of this invention, could determine the DNA sequence of the entire gene and the deduced amino acid sequence of the protein expressed from said gene. Therefore, the present invention encompasses the sequence of the gene in whole or in part.

In a further process embodiment of the present invention, the Aspergillus host cell may be further transformed with DNA sequences encoding a promoter sequence which is functionally recognized by the Aspergillus host and which is operably linked to the DNA sequence encoding the signal sequence. Additionally, the host cell may be transformed with a DNA sequences encoding a selectable marker expressible in the host cells. For example, the pyrG DNA sequence from *A. oryzae* which is expressible in *A. oryzae* (deRioter-Jacobs, Y.M.J.T., et al., *Curr. Genet.* (1989) 16:159–163).

In an embodiment of this invention, the *A. oryzae* strain is transformed with necessary DNA such that the lactase product is expressed and thereafter secreted from the Aspergillus host cell.

BRIEF DESCRIPTION OF THE FIGURES

FIG. 1 shows a schematic of the mutagenesis process resulting in CCC161 from CCC28 (CB587972 deposited in the Netherlands).

FIG. 2 shows a southern hybridization gel confirming a 9 kb BglII fragment from *A. oryzae* chromosomal DNA containing the lactase gene.

FIG. 3 shows a restriction map of the *A. oryzae* lactase fragment.

FIGS. 4a–c show the partial sequence for the *A. oryzae* lactase gene (Seq ID No 1). The figures show the presence of 8 introns in the gene sequence. The signal sequence for secretion of lactase is codons 314 to 370, inclusive (Seq ID No 4). The amino acid sequence of the signal sequence is shown in Seq ID No 3.

FIG. 5 shows a southern hybridization gel confirming the presence of pyrG gene from *A. oryzae* from 4 kb BamHI chromosomal fragment.

FIG. 6 shows a restriction map of the *A. oryzae* pyrG fragment.

FIG. 7 shows the formation of plasmid pPyrLac4 using pyrG11 and pUC218::A.o.lac plasmids.

FIG. 8 shows how the pPyrLac4 plasmid with KpnI releases a 12 kb fragment made up only of *A. oryzae* DNA and containing both the pyrG and lactase genes.

DETAILED DESCRIPTION OF THE INVENTION

The present invention demonstrates the enhanced production of lactase from a filamentous fungi, preferably *Aspergillus oryzae*. Specifically, this invention demonstrates the enhanced production of *A. oryzae* lactase in *A. oryzae* host strains. More particularly, about a ten fold increase in secreted lactase levels has been achieved by the processes described herein. This result was surprising in that little is known about the regulation of the lactase gene expression and, therefore, it was not expected that insertion of multiple copies (more than one) of the gene would result in overproduction of lactase, and particularly about a ten fold increase in production of lactase.

The enhanced production of such lactase is believed to be caused by the transformation of the host strain with more than one copy (multiple copies) of the lactase gene. The multiple copies of the lactase gene may be carried on a plasmid or vector containing the DNA sequence encoding the lactase gene, as well as other regulatory DNA, or may be on a linear fragment of DNA (as exemplified herein). Upon transformation of the Aspergillus host with such multiple copies of the lactase gene, the gene may be integrated into the chromosome of the host cell or may be carried extrachromosomally.

Following the teachings of this invention, biologically active lactase may be expressed and secreted from certain filamentous fungi, preferably Aspergillus and most preferably *A. oryzae*. Biologically active lactase as used herein means lactase secreted in active form as evidenced by its ability to mediate the biochemical activity mediated by its naturally occurring counterpart.

In general, a DNA fragment containing DNA encoding a signal sequence operably linked to a sequence encoding lactase is used. FIG. 4 (Seq ID No 1) encompasses the signal sequence at codons 314 to 370 inclusive. The DNA sequence for the secretion signal is shown in Seq ID No 4. The mature protein is coded for by the DNA sequence starting at codon 371.

The DNA fragment of the present invention may further comprise a selectable marker and/or a functional promoter and terminator sequence. The thus constructed DNA fragment, or a plasmid bearing such DNA, can be used to transform *A. oryzae*. Viable transformants may thereafter be identified by screening for the expression and secretion of lactase, or alternatively for the expressible selectable marker. Examples of suitable selectable markers include resistance to various antibiotics (e.g., aminoglycosides, phleomycin, benomyl, etc.) and sequences encoding *A. oryzae* pyrG, or sequences encoding pyrA, argB, trpC or amdS from *Aspergillus sp.*, pyr4 from *Neurospora crassa*, etc.; these and many other selectable markers are known to those skilled in the art.

Transformation is a known process for transferring genetic material into a host microorganism. Specifically, transformation means introducing DNA into an organism so that the DNA is maintained, either as an extrachromosomal element or chromosomal integrant. The transformation method used in the examples of the present invention was substantially as published by Campbell, E. I., et al., *Curr. Genet.* (1989) 16:53–56.

In a preferred embodiment of the process aspect of the present invention, no heterologous DNA is introduced into the host strain. The insertion of heterologous or foreign DNA sequences into a strain designated for commercial production would require more extensive testing before approval by regulatory organizations than if only homologous DNA were inserted. Homologous DNA means DNA derived from the host strain (preferably *A. oryzae*) or which is synthesized to conform to the DNA sequence of the host strain (i.e., *A. oryzae*) and which contains no more than 50 base pairs of contiguous synthetic DNA and preferably no more than 25 base pairs of contiguous synthetic DNA. According to current guidelines, "incorporation of fully sequenced DNA of 25 base pairs or less is not considered to comprise modifications to host vector systems". (U.S. Department of Health, Education, and Welfare, Public Health Service, National Institute of Health, "Modification of Certified Host-Vector Systems", *Recombinant-DNA Technical Bulletin* 2 (3):132, 1979.)

The host strain of the present invention may be any filamentous fungi and preferably is *A. oryzae*. Filamentous fungi are eukaryotic microorganisms and include all filamentous forms of the subdivisions Eumycotina. (Alexopoulos, C. J., 1962, *Introductory Mycology*, John Wiley & Sons, Inc., New York). Various species of filamentous fungi may be used as expression hosts (host strains) including the following genera: Aspergillus, Trichoderma, Neurospora, Podospora, Mucor, Achlya, Schizophylum, Ustilago and Coprinus. Specific expression hosts include *A. nidulans, A. niger, A. awamori, A. oryzae, N. crassa, T. reesei (longebrachiatum)* and *T. viride*. Suitable host strains are described in U.S. patent applications Ser. Nos. 07/413,010 and 07/770,049, which are incorporated herein by reference.

As used herein, a promoter or promoter sequence is a DNA sequence which is recognized by the particular filamentous fungi host strain for expression purposes (for example, a DNA sequence recognized by *A. oryzae*). The promoter sequence may be operably linked to a DNA sequence encoding the desired lactase product. Such linkage comprises positioning the promoter with respect to the initiation codon of the DNA sequence encoding the signal sequence of the transformation vector. The promoter sequence contains transcription and translation control sequences which mediate the expression of the signal sequence and the desired lactase product. Examples include the promoter from *A. niger* glucoamylase, the *A. niger* amylase promoters, and other promoters as known to those skilled in the art. Suitable promoters are described in U.S. patent application Ser. No. 07/413,010, which is incorporated herein by reference.

A signal sequence is an amino acid sequence which when operably linked to the amino-terminus of lactase permits the secretion of the lactase from the host strain. Such signal sequences may be the signal sequence normally associated with the lactase (i.e., the native signal sequence) or may be derived from other sources (i.e., foreign signal sequence). Signal sequences are operably linked to the lactase either by utilizing a native signal sequence or by joining a DNA sequence encoding a foreign signal sequence to a DNA sequence encoding the lactase in the proper reading frame to permit translation of the signal sequence and lactase product. The preferred signal sequences used in the present invention is the native signal sequence from *A. oryzae* lactase, which is shown in Seq ID No 4. The amino acid sequence of said signal (or secretion) sequence is shown in Seq ID No 3.

The disclosed preferred embodiments are presented by way of example and are not intended to limit the scope of this invention.

Experimental

Example 1

A. oryzae Strain Development

The strain used for lactase production is a derivative of CBS87972 originally obtained from the Centraal Bureau van Schimmelculture in the Netherlands. It was renamed CCC28 and produced approximately 5 U/ml lactase (1 U is that quantity of enzyme that will liberate 1 µmol of nitrophenol per min at 37° C. from ONPG under conditions described in the FCC Standard Lactase Activity Assay). As outlined in FIG. 1, CCC28 was subjected to a round of UV mutagenesis and selection, ultimately resulting in strain CCC161, which was deposited in accordance with the Budapest Treaty on May 13, 1995 as ATCC accession number 74285 with the American Type Culture Collection at 12301 Parklawn Drive, Rockville, Md., 20852, USA. Subject to 37 CFR 1.808(b), all restrictions imposed by the depositor on the availability to the public of the deposited material will be irrevocably removed upon granting of the patent.

---

Media

Culture maintenance was done on potato dextrose agar (PDA), DIFCO Products.
To get isolated colonies, cultures were done on PDA supplemented with sodium desoxycholate (180 mg/l) as inhibition of radial growth (PDA Nadx).
Solid production media Wheat bran 50 g
Agar agar (Difco) 17 g
Tap water 1:1
Liquid production media Wheat bran 50 g
Tap water 1:1
Germinative media Malt extract (Difco) 30 g
Distilled water 1:1
Solution A: To prepare conidial suspension for UV mutagenesis and inoculated liquid culture Tween 80 (Prolabo) 1 ml
Glycerol (Prolabo) 150 ml
$H_2O$ distilled to 1:1
Solution B: Conidial suspension for NTG mutagenesis Tween 80 1 ml
Malt extract 30 g
Distilled $H_2O$ 1:1
Solution C: Rinse solution for NTG mutagenesis Malt extract 30 mg
Glycerol 150 ml
Distilled water to 1:1

---

Solution D: Treatment solution for NTG mutagenesis

Tween 80 1 ml
TAPS (Sigma) 0,1 M
Distilled water 1:1
pH adjusted to 9

---

All the media and suspension were sterilized 20 min at 120° C. except those with glycerol which were sterilized 30 min at 110° C.

UV Mutagenesis

A conidial suspension in Solution A was prepared from a well sporulated PDA plate aged about 1 to 2 weeks. After decantation, to eliminate the mycelial fragments, the supernatant was taken; 4 ml of that conidial suspension was introduced in a small petri dish.

This suspension was used for irradiation. The petri dish was opened under a Philips germicid lamp (6 W) at 5 cm. Irradiation time was chosen to get a survival rate around 1%.

During irradiation the conidial suspension was agitated to get a homogeneous treatment.

After irradiation a sample of the irradiated conidial suspension was spread in the appropriate dilution on media to get isolated colonies to determine the survival rate. The other irradiated conidia were stored in a freezer at −20° C. for further analysis. After irradiation all the experiments were performed in the dark to inhibit the photorestoration system.

This resulted in strain CCC159, which produced ~18 U/ml lactase on solid media and 3 U/Ml in liquid culture. Subsequently, strain CCC159 was subjected to a round of NTG mutagenesis and selection, resulting in strain CCC161, which is capable of producing ~50 U/ml lactase in liquid culture. NTG mutagenesis was performed as described below:

NTG Mutagenesis

A conidial suspension was prepared as for UV mutagenesis Solution B (above). 5 ml of that suspension were introduced in an Erlenmeyer flask containing 20 ml of germinative media and incubated 3 hours at 30° C. on a rotary shaker.

Conidia were harvested by centrifugation, 15 min on a JOUAN bench centrifuge C400 at 4500 rpm. Conidia were resuspended in 25 ml of treatment Solution D (above). 8 ml of the conidial suspension were then introduced in an Erlenmeyer flask containing NTG crystals in an appropriate amount. For each experiment, 2 different NTG doses were tested and a control without NTG. Erlenmeyer flasks were incubated about 1 hour on a rotary shaker. Then, the conidia were washed twice by centrifugation and resuspended in 8 ml of rinse Solution C (above).

A sample of the final suspension was used for survival determination as in the UV procedure. The leftover was stored in a freezer at −20° C. for further analysis. The treated conidia were spread in the appropriate dilution on PDA Nadx. After 4 days incubation at 30° C. colonies were counted to determine the survival rate. After the survival rate was determined an appropriate amount of treated conidia were spread in dilution on PDA Nadx to get enough survivors to test for lactase activity.

It was necessary to do a subcloning step after mutagenesis to separate the parental type from the mutant types. For that purpose a conidial suspension of the "mutant" was spread in appropriate dilution to get isolated colonies, to be sure one colony was originated from one conidia. For each mutant, 100 subclones were tested for lactase activity in solid culture. Best subclones were re-picked on PDA media and tested liquid culture.

Example 2

Cloning *Aspergillus oryzae* Lactase

The lactase cDNA sequence from *A. niger* is known and has been published (Kumar, V., et al., *Bio/Technology*

10:82–85, 1992). To identify a fragment of *A. oryzae* CCC161 chromosomal DNA large enough to contain the lactase gene including any necessary sequences for transcription, translation and secretion, probes were generated by PCR based on the *A. niger* sequence using *A. niger* DNA as a template. Using these probes, a 9 kb BglII fragment from *A. oryzae* chromosomal DNA containing the lactase gene was identified by southern hybridization (FIG. 2). A subgenomic library of BglII cut chromosomal DNA encompassing this size class was constructed in pUC218 and an individual clone (pUC218::A.o.lac) containing the lactase gene was identified by colony hybridization using the probes described above. A restriction map of the fragment was generated (FIG. 3) and sequencing of the gene is in progress. The partial sequence of the gene is provided in FIG. 4 (Seq ID No 1), which includes introns present in the gene. The partial deduced amino acid sequence of the protein expressed by the *A. oryzae* lactase gene is set forth as Seq ID No 2.

Example 3

Cloning *Aspergillus oryzae* pyrG

The pyrG gene of *Aspergillus oryzae* is known to reside on a 4 kb BamHI chromosomal fragment (deRioter-Jacobs, Y.M.J.T., et al., *Curr. Genet.* 16:159–163, 1989). This was confirmed by southern hybridization to BamHI digested *A. oryzae* chromosomal DNA using probes generated by PCR, based on the *A. niger* sequence using *A. niger* DNA as a template (FIG. 5). A subgenomic library of BamHI cut chromosomal DNA encompassing this size class was constructed in pUC18 and an individual clone (pyrG11) containing the pyrG gene was identified by colony hybridization using the probes described above. A restriction map of the fragment was generated (FIG. 6) confirming its identity.

Example 4

Construction of pPyrLac4

The two plasmids described above (pyrG11 and pUC218::A.o.lac) were used to construct the plasmid pPyrLac4 in the following manner (FIG. 7):

(1) pyrG11 was cut with KpnI and BamHI and the fragment containing pyrG was isolated and cloned into KpnI and BamHI cut pUC19 resulting in the plasmid pyrGKB. This plasmid has a unique BglII site within the *A. oryzae* pyrG fragment but external to the pyrG gene.

(2) pUC218::A.o.lac was digested with BglII and the *A. oryzae* fragment containing the lactase gene was isolated and cloned into the unique BglII site in pyrGKB resulting in the plasmid pPyrLac4. pPyrLac4 was subsequently cut with KpnI, releasing a 12 kb fragment made up of only *A. oryzae* DNA and containing both the pyrG and lactase genes (FIG. 8). This fragment was used to transform *A. oryzae* CCC161pyr6 to increase lactase production.

Example 5

Transformation of *A. oryzae* CCC161

In order to use the above DNA fragment for transformation into our production strain, a pyrG mutant of CCC161 was prepared. The pyrG mutant was prepared using a modification of the procedure described by Mattern, I. E., et al., *Mol. Gen. Genet.* 210:460–461, 1987, by selecting for a spontaneous mutant resistant to 5-fluoro-orotic acid (5-FOA) and subsequently screening for colonies that required Uridine for growth. One such mutant, CCC161pyr6, was used for further development.

The KpnI fragment described above was used to transform CCC161pyr6 using the method described by Campbell, E. I., et al., *Curr. Genet.* 16:53–56, 1989, with minor modifications. Transformants which had incorporated the pyrG gene and no longer required Uridine for growth were tested for their ability to produce lactase. The screen for enhanced lactase production employed the use of X-gal (5-bromo-4-chloro-3-indol-β-D-galactoside) indicator plates, a standard method used for the detection of β-galactosidase activity in *E. coli*, as described below and in *Advanced Bacterial Genetics*, Davis, R. W., Botstein, D. and Roth, J. R. eds., Cold Spring Harbor Laboratory, p. 48, 1980, with media modifications.

| X-Gal Detection Plates | |
|---|---|
| | L |
| NaNO3 | 6 gr |
| KCl | 0.52 gr |
| KH$_2$PO$_4$ | 1.52 gr |
| Wheat Flour | 10 gr |
| Trace Elements | 1.0 ml |
| pH to 6.5 with NaOH | |
| Bacto-Agar | 20 gr |
| Autoclave | |
| Add 1.25 ml 20% MgSO$_4$/500 ml | |
| 500 μl antibiotics/500 ml | |
| 50 μg/ml final concentration of X-gal (with IPTG 1 mM final concentration) (283 mg IPTG + 50 mg X-gal + 2 ml DMF, wait to go into solution then add 8 ml sterile water. This is enough for 1 L.) | |
| Add glucose at various concentrations (1% for a standard screen) | |
| Pour plates | |
| Make big patches of spores on plate | |
| Check color after 2–3 days at 30° C. or 37° C. | |

Table I below shows the results of the first round of transformant screening on plates and in liquid culture.

TABLE I

Transformation Results
Host Strain: CCC161
Plasmid: pPyrLac4

| Colony # | Shake U/ml | 14 Liter U/ml | Blue |
|---|---|---|---|
| 1 | 18 | NT | − |
| 2 | 56 | NT | − |
| 3 | 101 | NT | − |
| 4 | 405 | 890 | + |
| 5 | 80 | NT | − |
| 6 | 38 | NT | − |
| 7 | 44 | NT | − |
| 8 | 47 | NT | − |
| 9 | 114 | NT | − |
| 10 | 39 | NT | − |
| 11 | 21 | NT | − |
| 12 | 7 | NT | − |
| 13 | 51 | NT | − |
| 14 | 14 | NT | − |
| 15 | 28 | NT | − |
| 16 | 55 | NT | − |
| 17 | 207 | NT | − |
| 18 | 286 | 500 | + |
| 19 | 96 | NT | − |
| 21 | 648 | 750 | + |

NT = Not Tested

After repeated testing both in shake flasks and 14 liter fermenters, colony #4 proved to be the most consistent lactase producer, routinely reaching levels >500 U/ml in shake flask experiments and in 14 liter fermenters, and was designated Lac4. A comparison of Lac4 to the parental strain CCC161 by southern hybridization using the labelled lactase gene as a probe to BamHI cut chromosomal DNA indicated an increase in the number of lactase gene copies in the transformed strain (FIG. 8). When pUC19 DNA was used as a probe no hybridization was detected, indicating the absence of any foreign DNA.

What is claimed is:

1. A DNA fragment encoding a protein having lactose hydrolytic activity isolated from *Aspergillus oryzae* comprising the sequence shown in Seq ID No 1.

2. An expression vector comprising the DNA fragment of claim 1.

3. A host cell transformed with the expression vector of claim 2.

4. An Aspergillus host cell transformed with the expression vector of claim 2.

5. The *Aspergillus oryzae* host cell ATCC #74285 transformed with the expression vector of claim 2.

6. A method of enhancing the production of lactase in an *Aspergillus oryzae* host cell comprising:

a) transforming the host cell with DNA comprising a DNA sequence encoding *A. oryzae* lactase and a DNA sequence encoding native *A. oryzae* lactase signal sequence operably linked to the DNA sequence encoding the *A. oryzae* lactase;

b) culturing the transformed cells of step a) under suitable conditions to take up the DNA and form transformants therewith; and c) screening the transformants for enhanced lactase production.

7. A method of claim 6 wherein the host cell is transformed with more than one copy of DNA encoding *A. oryzae* lactase.

8. A method of claim 6 wherein the host cell is transformed with DNA further comprising a DNA sequence encoding a selectable marker expressible in Aspergillus.

9. A method of claim 8 wherein the selectable marker is the *Aspergillus oryzae* pyrG gene.

10. A method of claim 6 comprising transforming an *Aspergillus oryzae* host cell with DNA encoding the *Aspergillus oryzae* lactase (Seq ID No 1), DNA encoding an *Aspergillus oryzae* signal sequence (Seq ID No 4) and DNA encoding an *Aspergillus oryzae* selectable marker.

* * * * *